United States Patent [19]

Ghoneum et al.

[11] Patent Number: 5,560,914

[45] Date of Patent: Oct. 1, 1996

[54] IMMUNOPOTENTIATOR AND METHOD OF MANUFACTURING THE SAME

[75] Inventors: Mamdooh H. Ghoneum, Los Angeles, Calif.; Hiroaki Maeda, Matsudo, Japan

[73] Assignee: Daiwa Pharmaceutical Co., Ltd., Toyko, Japan

[21] Appl. No.: 501,751

[22] Filed: Jul. 12, 1995

[51] Int. Cl.$^6$ ............................. A61K 35/78; C12N 1/14
[52] U.S. Cl. .................... 424/195.1; 435/254.1; 435/256.1; 435/911; 424/94.61; 424/274.1; 424/278.1
[58] Field of Search ............................. 435/254.1, 256.1, 435/911; 424/278.1, 274.1, 94.61, 195.1

[56] References Cited

FOREIGN PATENT DOCUMENTS 1153701  6/1989  Japan .

Primary Examiner—John W. Rollins
Attorney, Agent, or Firm—Townsend and Townsend and Crew

[57] ABSTRACT

In a method of producing an immunopotentiator, a plant tissue material is extracted with hot water, the insoluble material is filtered, and the filtrate thereof is treated with glucoamylase to decompose a starch, thereby obtaining a water-soluble polysaccharide. Ammonium sulfate is added in a culture filtrate obtained by culturing any one of Asp Oryzae of the Aspergillaceae and Lentinus edodes of the Basidiomycetes to obtain an enzyme complex from the precipitate. The water-soluble polysaccharide and the enzyme complex are added together to cause them to react at a pH of 4.5 for 30 to 60 minutes and then at a pH of 6.0 for 30 to 60 minutes, thereby biologically modifying the water-soluble polysaccharide.

3 Claims, No Drawings

IMMUNOPOTENTIATOR AND METHOD OF MANUFACTURING THE SAME

BACKGROUND OF THE INVENTION

The present invention relates to an immunopotentiator and a method of modifying a water-soluble polysaccharide of a plant tissue material such as a Poaceae plant and particularly rice bran using an enzyme complex produced by the Hyphomytes so as to obtain the immunopotentiator.

Immunopotentiators have a variety of applications as foodstuffs and drugs. It is known that aging and stress lower the animal immunity and as such we easily suffer from various diseases. A new branch of nutritional chemistry which tries to fortify human immunity by improving the daily diet is in a new stage of development in consideration of the importance of preventive medicine. In a cancer therapy, the use of an immunopotentiator with a chemotherapeutic drug and radiotherapy has demonstrated an excellent therapeutic effect.

The present inventor found effectiveness of modification of a natural material using the Hyphomytes in developing and activating natural killer cells (NK cells) in the human immune system.

There is already known a method of metabolizing a natural material, i.e., a plant fiber material in a culture solution (Japanese Patent Laid-Open No. 1-153701). In this prior art, rice bran is used as the material. The rice bran is degreased and denigninized and is treated with a low-concentration alkali, thereby producing rice bran crude hemicellulose. By using this substance, the Hyphomytes is cultured to metabolize and partially decompose the hemicellulose.

The material obtained by the above method is expected to have various effects on human body. In the above method, however, since the plant fiber material is obtained by metabolization, a product with a stable quality cannot be obtained. The resultant product is not sufficient in production efficiency activity of the NK cells. In the above method, it takes much time to culture the Hyphomytes. This method is not always appropriate as an industrial manufacturing method.

SUMMARY OF THE INVENTION

It is an object of the present invention to provide a stable material capable of producing and activating NK cells and possibly other white blood cell populations, and a method industrially used to manufacture this material.

In order to achieve the above object of the present invention, there is provided a method of producing an immunopotentiator, comprising the steps of 1) extracting a plant tissue material with hot water, filtering an insoluble material, and treating a filtrate thereof with glucoamylase to decompose a starch, thereby obtaining a water-soluble polysaccharide, 2) adding ammonium sulfate in a culture filtrate obtained by culturing any one of Asp Oryzae of the Aspergillaceae and Lentinus edodes of the Basidiomycetes to obtain an enzyme complex from a precipitate thereof, and 3) adding the water-soluble polysaccharide obtained in step 1) and the enzyme complex obtained in step 2) together to cause them to react at a pH of 4.5 for 30 to 60 minutes and then at a pH of 6.0 for 30 to 60 minutes, thereby biologically modifying the water-soluble polysaccharide obtained in step 1).

As described above, the step of obtaining a water-soluble polysaccharide of a plant tissue and the step of obtaining an enzyme complex are independently performed under given conditions. The biological modification of the present invention is performed by an enzyme reaction and hydrolysis using a carbohydrase. For this reason, the resultant material has predetermined constituting saccharides, and its activity is stable. The step of obtaining an enzyme complex, which requires the culture step for 10 to 14 days is performed independently of the step of obtaining a water-soluble polysaccharide of a plant tissue. The enzyme complex can be prepared in advance, thereby shortening the manufacturing time and reducing the cost.

In addition, the material obtained by the method of the present invention is xylane mainly having a $\beta$-1.4 xylopyranose chain. In the present invention, since no material which decomposes the xylose bond is contained, the above enzyme is used to hydrolyze bonds except for the xylose bond, and only the xylose bond is left. Therefore, according to the method of the present invention, when the biological modification progresses, the xylose content becomes high.

DESCRIPTION OF THE PREFERRED EMBODIMENT

Five liters of water were added to 1,000 g of rice bran, the resultant mixture was subjected to extraction with hot water at 100° C. for 60 minutes, and the insoluble product was filtered. The starch in the filtrate was hydrolyzed to obtain a water-soluble polysaccharide extract of the rice bran.

Any hemicellulose can be used in place of rice bran. In particular, the hemicellulose of a Poaceae plant is excellent.

In this embodiment, two types of enzyme complexes were produced. One is an enzyme complex obtained by culturing Asp Oryzae of the Aspergillaceae, and the other is Lentinus edodes of the Basidiomycetes.

Medium compositions for these products are as follows.

| 1) Medium Composition for Asp Oryzae | |
|---|---|
| Distilled water | 1 l |
| Glucose | 40 g |
| Peptone | 6 g |
| $KH_2PO_4$ | 0.1 g |
| NaCl | small amount |
| $CaCl_2$ | small amount |
| $FeCl_3$ | small amount |
| The culture conditions are pH 3.5, 30° C., and 14 days. | |
| 2) Medium Composition for Lentinus Edodes | |
| Distilled water | 1 l |
| Sucrose | 5 g |
| $Na_4VNO_3$ | 10 g |
| $KH_2PO_4$ | 5 g |
| $MgSO_4$ | 2.5 g |
| $FeSO_4$ | small amount |
| The culture conditions are pH 4.5, 20° C., and 14 days. | |

After the culture in these media, ammonium sulfate was added to each culture filtrate to achieve 50% saturation. The resultant precipitates were filtered to obtain an Asp Oryzae enzyme complex (Enzyme-AO) and a Lentinus edodes enzyme complex (Enzyme-LE).

Finally, 3 g of the Enzyme-AO were added to 4.5 l of the water-soluble polysaccharide extract of the rice bran. After adjusting the pH of the solution to 4.5, the solution was reacted at 40° C. for 30 minutes. After the pH of the solution was re-adjusted to 6.0, the reaction was continued for 30 minutes to prepare a rice bran water-soluble polysaccharide (RBX-AO) modified with an Asp Oryzae exoenzyme. Similarly, the Enzyme-LE was added to the water-soluble polysaccharide extract of rice bran, and the resultant solution was subjected to a reaction to obtain a rice bran water-soluble polysaccharide (RBX-LE) modified with a Lentinus edodes exoenzyme. Each of the resultant materials contains xylane having a β-1.4 xylopyranose chain as a main component.

Each product can be sterilized and condensed to be directly used as a liquid drug. In addition, the product is granulated by freeze-drying or spray-drying into a tablet or granule.

The physicochemical characteristics of the RBX-AO and RBX-LE are as follows:

| Average Molecular Weight | RBX-AO 650,000 dalton | | RBX-LE 600,000 dalton | |
|---|---|---|---|---|
| Constitutive Saccharide | arabinose | 22% | arabinose | 26% |
| | xylose | 54% | xylose | 48% |
| | galactose | 5% | galactose | 7% |
| | glucose | 6% | glucose | 6% |
| | mannse | 8% | mannse | 9% |
| | others | 5% | others | 4% |

The activity of NK cells of patients was measured to determine the effects of the above RBX-LE and RBX-AO. To eliminate the influences of other drugs, administration of all drugs was inhibited for one month before the measurement. Six grams of the RBX-LE were orally administered for each patient per day. The activity of the NK cells was 34.5 LU in the beginning. The activity rose to 66.5 LU in two weeks. Even if the administration was stopped, the activity was kept at high level (64 LU) for two months. The same result was obtained for the RBX-AO.

The xylose contents can be measured to determine the progress of the enzyme reaction. The contents of the RBX-LE and RBX-AO with respect to 4.5 l of the rice bran extract, which exhibited the maximum values of the xylose contents, were measured, and the results are summarized below. As in the above embodiment, the products were reacted at a pH of 4.5 and 60° C. for 30 minutes and at a pH of 6.0 for 30 minutes.

| Xylose Content for RBX-AO | |
|---|---|
| 1.5 g | 38% |
| 3.0 g | 48% |
| 4.5 g | 49% |
| 6.0 g | 48% |
| Xylose Content for RBX-LE | |
| 1.5 g | 31% |
| 3.0 g | 43% |
| 4.5 g | 44% |
| 6.0 g | 44% |

As described above, the maximum xylose content is obtained at a 3.0 g RBX-LE or RBX-AO content. Even if the RBX-LE or RBX-AO is added in an amount exceeding 3.0 g, the xylose content does not increase any longer.

The examination result for the reaction time is as follows. The time represents periods during which the examination was performed at pHs of 4.5 and 6.0.

| Time (min) | 30 | 60 | 90 | 120 |
|---|---|---|---|---|
| RBX-LE | 48% | 54% | 55% | 53% |
| RBX-AO | 43% | 48% | 49% | 48% |

In any case, the maximum value is obtained in 60 minutes, and the xylose content does not increase further even if the reaction is continued exceeding 60 minutes.

As described above, the step of obtaining a water-soluble polysaccharide of a plant tissue and the step of obtaining an enzyme complex are independently performed under given conditions. The biological modification of the present invention is performed by an enzyme reaction and hydrolysis using a carbohydrase. For this reason, the resultant material has predetermined constitutive saccharides, and its activity is stable. The step of obtaining an enzyme complex, which requires the culture step for 10 to 14 days is performed independently of the step of obtaining a water-soluble polysaccharide of a plant tissue. The enzyme complex can be prepared in advance, thereby shortening the manufacturing time and reducing the cost.

In addition, the material obtained by the method of the present invention is xylane having a β-1.4 xylopyranose chain. It contains a large amount of xylose to produce and activated NK cells and possibly other cell populations such as T and B cells.

What is claimed is:

1. A method of producing an immunopotentiator, comprising the steps of:

1) extracting a plant tissue material from a member of the plant family Poaceae with hot water, filtering an insoluble material, and treating a filtrate thereof with glucoamylase to decompose the starch, thereby obtaining a water-soluble polysaccharide;

2) adding ammonium sulfate in a culture filtrate obtained by culturing any one of Asp Oryzae of the Aspergillaceae and Lentinus edodes of the Basidiomycetes to obtain an enzyme complex from a precipitate thereof; and 3) adding the water-soluble polysaccharide obtained in step 1) and the enzyme complex obtained in step 2) together to cause them to react at a pH of 4.5 for 30 to 60 minutes and then at a pH of 6.0 for 30 to 60 minutes, thereby biologically modifying the water-soluble polysaccharide obtained in step 1) and producing an immunopotentiator.

2. An immunopotentiator produced by the method of claim 1.

3. The method of claim 1, wherein the plant tissue material is rice bran.

* * * * *